United States Patent [19]

Crivello

[11] Patent Number: 5,079,378
[45] Date of Patent: Jan. 7, 1992

[54] PREPARATION OF DIARYLIODONIUM SALT PHOTOINITIATORS HAVING LONG CHAIN ESTER GROUPS CONCATENATED WITH ARYL GROUPS

[75] Inventor: James V. Crivello, Clifton Park, N.Y.

[73] Assignee: Polyset Corporation, Mechanicville, N.Y.

[21] Appl. No.: 558,627

[22] Filed: Jul. 27, 1990

[51] Int. Cl.$^5$ .......................... C07F 9/02; C07F 5/02; C07F 9/66; C07F 9/90
[52] U.S. Cl. .......................... 556/64; 556/1; 534/11; 568/8
[58] Field of Search .......................... 556/7, 13, 64, 1; 427/54.1; 430/280, 447, 919; 522/15, 25, 129, 170; 204/159.18, 181.6; 428/413; 560/3, 8, 51; 534/11; 568/8

[56] References Cited

U.S. PATENT DOCUMENTS

| | | | |
|---|---|---|---|
| 4,090,936 | 5/1978 | Barton | 204/159.18 |
| 4,399,071 | 8/1983 | Crivello et al. | 556/64 |
| 4,537,725 | 8/1985 | Irving | 556/64 X |
| 4,882,201 | 11/1989 | Crivello | 427/54.1 |

*Primary Examiner*—Arthur C. Prescott
*Attorney, Agent, or Firm*—Schmeiser, Morelle & Watts

[57] ABSTRACT

A highcarbon-containing diaryliodonium initiator for cationic polymerization which possesses enhanced solubility characteristics over conventional diaryliodonium initiators. By the disclosed process, a novel photo/thermal initiator is obtained which is uniquely characterized by the concatenation of a long chain ester with an aryl group, resulting in a total number of carbon atoms in the entire moiety attached to the iodine atom in excess of 20.

7 Claims, No Drawings

PREPARATION OF DIARYLIODONIUM SALT PHOTOINITIATORS HAVING LONG CHAIN ESTER GROUPS CONCATENATED WITH ARYL GROUPS

BACKGROUND OF THE INVENTION

1. Field of the Invention

Diaryliodonium salts are used as efficient photoinitiators for cationic polymerization. The instant invention relates generally to the synthesis of diaryliodonium salts possessing aliphatic ester groups of differing lengths and, specifically, to novel diaryliodonium salts in which long chain ester groups are attached to the aryl groups. More precisely, diaryliodonium salts of the instant invention possess aryl and aliphatic ester groups bonded to iodine which together comprise an aggregate of more than 20 carbon atoms.

2. Discussion of Relevant Art

A search of the patent literature, as well as the professional journals, reveals that diaryliodonium salts having the structure $Ar-I^+-Ar\ MX_n^-$, where Ar are aryl groups and $MX_n^-$ represents the metal halide anion, serve as efficient photoinitiators for cationic polymerization. In U.S. Pat. No. 4,090,936, issued to Barton for PHOTOHARDENABLE COMPOSITIONS, aforementioned diaryliodonium salts are disclosed wherein the aryl groups are defined as consisting of aromatic groups or arylalkyl groups containing from 6 up to, but not exceeding, 20 carbon atoms. Quite matter of factly, such salts as would contain more carbon atoms are specifically excluded. In a patent recently issued to the instant inventor and incorporated herein by reference: NON-TOXIC ARYL ONIUM SALTS, UV CURABLE COATING COMPOSITIONS AND FOOD PACKAGING USE (U.S. Pat. No. 4,882,201), the invention of non-toxic photoinitiators comprising diaryliodonium salts which possess alkoxy groups of differing lengths is taught. However, no mention is made of similar diaryliodonium salts containing other functional groups having long carbon chains. Most notably, diaryliodonium salts with ester (aliphatic) groups attached to the aryl moieties, together exceeding 20 carbon atoms, are not described therein, nor in the patent or chemical literature.

The instant inventor believed that the organic solubility of diaryliodonium salts could be enhanced if the total number of carbon atoms within the groups bonded to iodine exceeded 20. Quite unexpectedly, he discovered that it is possible to prepare, in good to excellent yield, diaryliodonium salts in which long chain ester groups are attached to the aryl groups, thus providing an aggregate (aromatic-aliphatic) number of carbon atoms in the desired quantities. Incorporation of the long chain ester functions onto the aryl groups does indeed confer enchanced solubility to these salts compared to their lower molecular weight counterparts, a characteristic hereinafter demonstrated.

STATEMENT OF THE INVENTION

A general process for the synthesis of the diaryliodonium salts of the instant invention is:

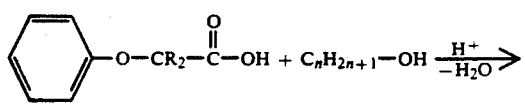

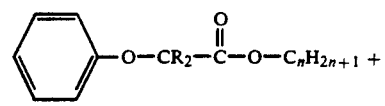

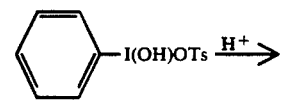

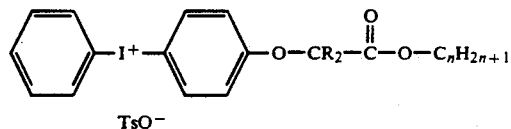

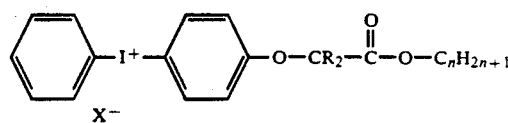

In the above process, the R groups represent hydrogen, alkyl, halogen or aryl. The values n represent integers such that the combined number of carbon atoms included by the entire moiety attached to the positively charged iodine atom is greater than 20. MX represents a metal halide and $X^-$ comprises those complex (metal) halide anions such as $BF_4^-$, $PF_6^-$, $AsF_6^-$, $SbF_6^-$, as well as anions of strong protonic acids such as $ClO_4^-$, $CF_3SO_3^-$, $FSO_3^-$, $CH_3SO_3^-$, and $C_4F_9SO_3^-$. Several examples of such compounds are:

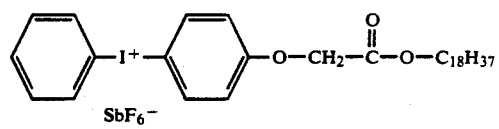

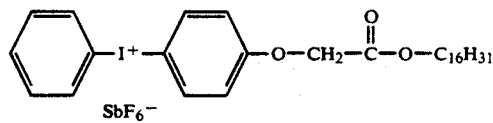

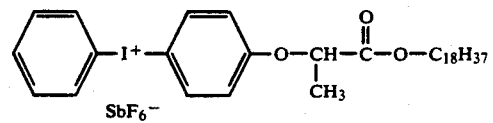

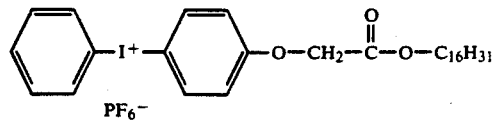

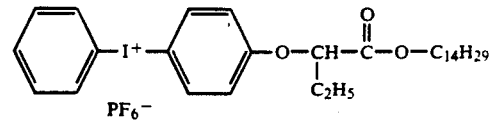

-continued

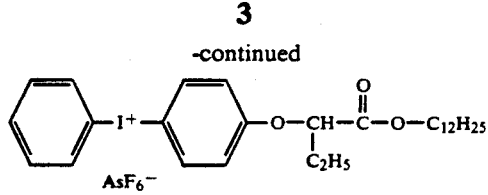
AsF₆⁻

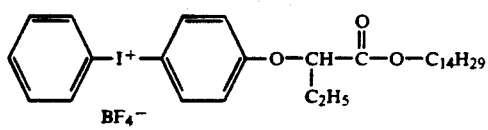
BF₄⁻

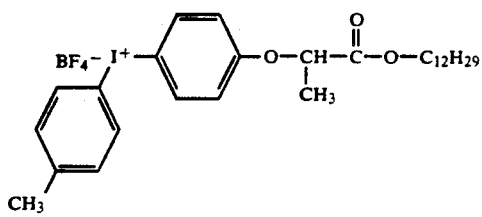
BF₄⁻

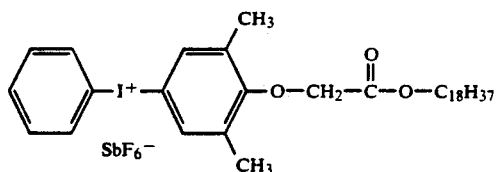
SbF₆⁻

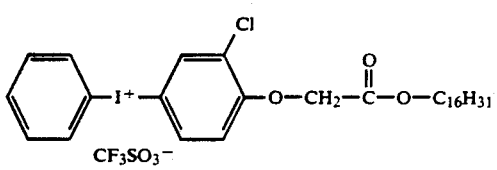
CF₃SO₃⁻

The initiators described in this disclosure may be used to carry out the photoinitiated polymerization of such cationically polymerizable monomers as momo, di and polyfunctional epoxides such as bisphenol-A diglycidyl ether, butanedioldiglycidyl ether, 3,4-epoxycyclohexyl-methyl-3', 4'-epoxycylohexane carboxylate, phenol novolac epoxides, poly (1,2- butadiene oxide), epoxidized soybean oil, epoxidized linseed oil; vinyl ethers, such as diethyleneglycol divinyl ether, triethyleneglycol divinyl ether, dicyclohexanediol divinyl ether, 1,4-butandiol divinyl ether; vinyl hydrocarbon monomers including styrene, alpha-methyl styrene, divinyl benzene, 1,3-diisopropenylbenzene, and acenaphthalene. Heterocyclic mononers such as N-vinyl carbazole, oxetane, trioxane, 1,3-dioxolane, and tetrahydrofuran can also be polymerized using these photoinitiators. The most useful, but not exclusive, application of these photoinitiators are in formulations intended for use as ultraviolet light (UV) curable coatings, adhesives and sealants. The photoinitiators are also useful for photoimaging purposes as in the fabrication of photoresists for electrical and electronic applications.

In addition, the same diaryliodonium salts are useful in combination with copper cocatalysts or free radical initiators as thermal initiators for the above monomers and polymers. These initiator/coinitiator combinations have utility in a wide variety of applications including molding. pulltrusion, composites, encapsulants, adhesives and foams.

The above is a general synthesis which can be expanded to cover a large family of such photoinitiators. This includes also hexafluorophosphate as well as hexafluoroantimonate containing salts. The photoinitiators are very reactive and, because of their high molecular weight and hydrocarbon-like character, are probably non-toxic. The reader is once again referred to U.S. Pat. No. 4,882,201, issued to the instant inventor.

The following accounts of actual experiments are given by way of demonstration and not of limitation.

PREPARATION OF [HYDROXY(TOSYLOXY)IODO]BENZENE (MW = 394)

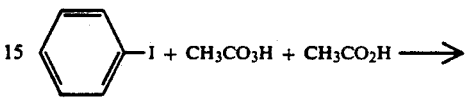

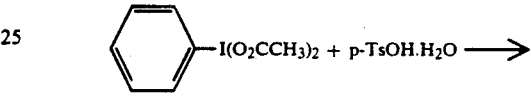

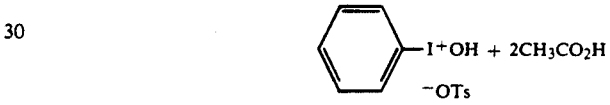

Initially, 208 g (1.0 mol, 98%) of iodobenzene were placed in a 1 L three necked flask fitted with an addition funnel, condenser, thermometer and paddle stirrer. Dropwise, 52 g. (2.4 mol) 35% peracetic acid were added, with stirring. The temperature was maintained between 40° and 45° C. during the addition using a water bath. After addition was complete, the yellow solution was maintained at 40° C. for one hour. Within 20 minutes a precipitate of iodosobenzene diacetate began to form and the solution became quite thick. Maintaining the reaction mixture at 40° C., there were added 298 g (1.57 mol) p-toluenesulfonic acid monohydrate in portions. As reaction proceeded, the solution became preceptively more fluid, then once again thixotropic as the product [hydroxy(tosyloxy)iodo]benzene precipitated. The reaction temperature was maintained at 40° C. for two hours after addition had been completed. The product was isolated by suction filtration, washed with water and air dried; thus, were obtained 217.3 g of the product (yields generally ranged from 84 to 97%).

EXAMPLE I PREPARATION OF

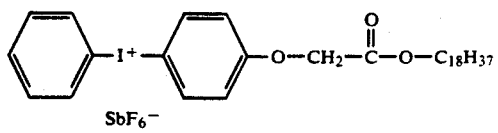
SbF₆⁻

SYNTHESIS OF 1-OCTADECYLPHENOXYACETATE

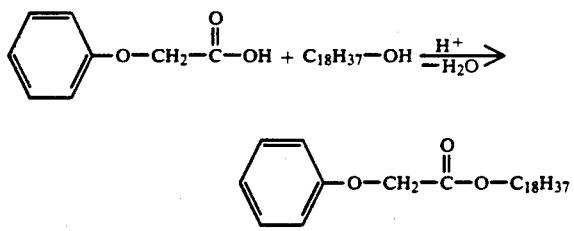

Into a 500 ml round bottom flask there were placed 15.2 g (0.1 mol) phenoxyacetic acid, 27 g (0.1 mol) 1-octadecanol, 110 ml toluene and 0.5 g p-toluenesulfonic acid monohydrate. The reaction was heated to reflux and the water separated using a Dean Stark trap. The reaction was allowed to proceed for 14 hours during which the theoretical amount of water (1.8 g) collected in the trap. Using the trap, the toluene was removed and the oil which remained cooled. The product ester crystallized on cooling. Quantitative yield of 41 g of the product was obtained having a m.p. of 50°-52° C. and molecular weight (MW) of 404 g/mol ($C_{26}H_{44}O_3$).

The above experiment was repeated using one mole each of 1-octadecanol and phenoxy acetic acid. There was also added 1 g p-toluene sulfonic acid and 250 ml toluene. The theoretical amount of water (18 ml) was obtained within three hours at reflux. The remaining toluene was removed on a rotary evaporator, giving a pale yellow oil.

SYNTHESIS OF (4(1-OCTADECYLPHENOXYACETATE))PHE- NYL IODONIUM HEXAFLUOROANTIMONATE

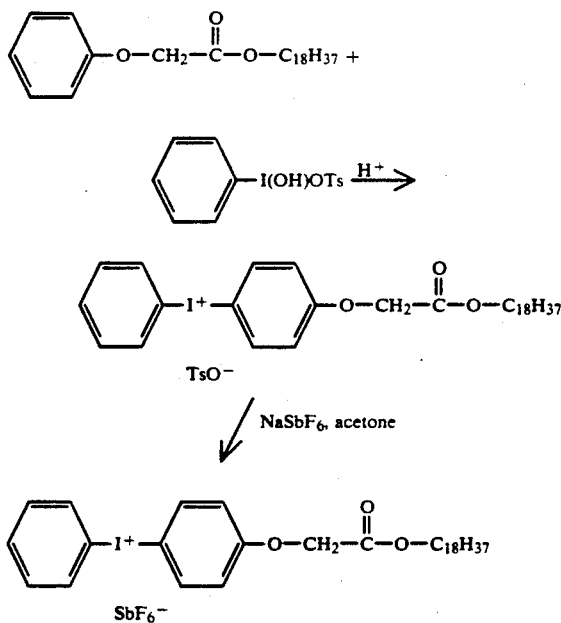

To a 100 ml Erlenmeyer flask, there were added 8.08 g (0.02 mol) of the above ester, 7.84 g (0.02 mol) hydroxytosyloxyiodobenzene, 20 ml methylene chloride and 5 ml glacial acetic acid. This reaction mixture was placed in a water bath and heated for two hours to complete the reaction. Next, the reaction mixture was gravity filtered and the solvent removed from the filtrate using a rotary vacuum evaporator. A pale yellow oil remained. To the oil there was added ≈40 ml acetone and 5.18 g sodium hexafluoroantimonate. Immediate metathesis took place with the formation of a precipitate of sodium tosylate as the reaction proceeded. After 15 min. stirring, the reaction mixture was gravity filtered and the acetone removed on a rotary evaporator. On cooling, partial crystallization of the product occured. When water was added to the semisolid product, the entire reaction mixture crystallized to give, after drying overnight at ≈40° C. in vacuuo, a pale yellow product. Yield was 10.2 g (60% theory) of M.W. 845 g/mol ($C_{32}H_{48}O_3ISbF_6$), m.p. 45°-47° C. Solvents comprised i-propanol, toluene, acetone and cyclohexane. The compound was purified by trituration of an i-propanol solution with distilled water.

The salt was an excellent photoinitiator for the polymerization of 4-vinyl cyclohexene dioxide. It is also soluble in epoxidized linseed oil, epoxidized soybean oil and in poly(1,2-butadiene oxide) and can be used to photopolymerize these substances.

Scale-up of the above reaction was carried out using 80.8 g (.2 mol) of the ester and 78.4 g (0.2 mol) of hydroxytosyloxyiodobenzene, 150 ml methylene chloride and 50 ml glacial acetic acid. The mixture was heated to reflux (40° C.) for two hours. The turbid solution was filtered and the solvent removed under vacuum. Then, 300 ml acetone was added, followed by 51.8 g (0.2 mol) sodium hexafluoroantimonate. The reaction was allowed to stir for one hour and was then filtered. On removal of the actone and the addition of a small amount of distilled water, partial crystallization took place. The product, a pale yellow oil was mixed with water and filtered. A semisolid product was obtained which was recrystallized by dissolution in hot isopropanol. Crystallization took place by cooling on ice and the product was isolated by filtration. There were obtained 107 g of the desired product.

The above reaction was repeated with a replacement of the $NaSbF_6$ with 3.68 g $KPF_6$, to prepare the corresponding iodonium hexafluorophosphate salt. After 1 hour at 40° C., the potassium tosylate was filtered off. However, the product tended to cocrystallize during the filtration. The product (10.4 g) was isolated on addition of distilled water to the filtrate. Higher yields could be obtained through direct addition of water to the acetone solution. A 3 mil film of a 1% solution of the above photoinitiator, dissolved in 4-vinylcyclohexene dioxide, cured after a 5 second exposure to ultraviolet lighting using a UVEXUS Spot cure apparatus.

EXAMPLE 2 PREPARATION OF

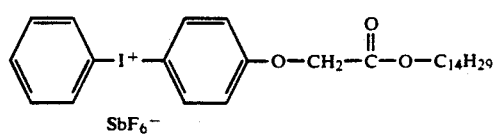

SYNTHESIS OF 1-TETRADECYLPHENOXYACETATE
(C$_{22}$H$_{36}$O$_3$, MW=348)

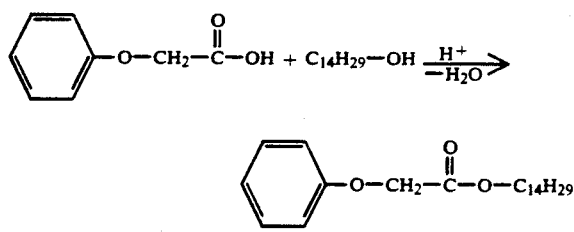

Into a 500 ml three neck flask equipped with a magnetic stirrer, reflux condenser and Dean Stark trap were placed 15.2 g (0.1 mol) phenoxyacetic acid, 21.6 g (0.1 mol) 1-tetradecanol, 1 g p-toluenesulfonic acid monohydrate and 100 ml toluene. The reaction mixture was brought to reflux and held at the temperature for four hours. The theoretical amount of water was collected in the trap. The toluene was distilled off and the product crystallized on standing.

SYNTHESIS OF (4(1-TETRADECYLPHENOXYACETATE))PHENYL IODONIUM HEXAFLUOROANTIMONATE (OPPA)

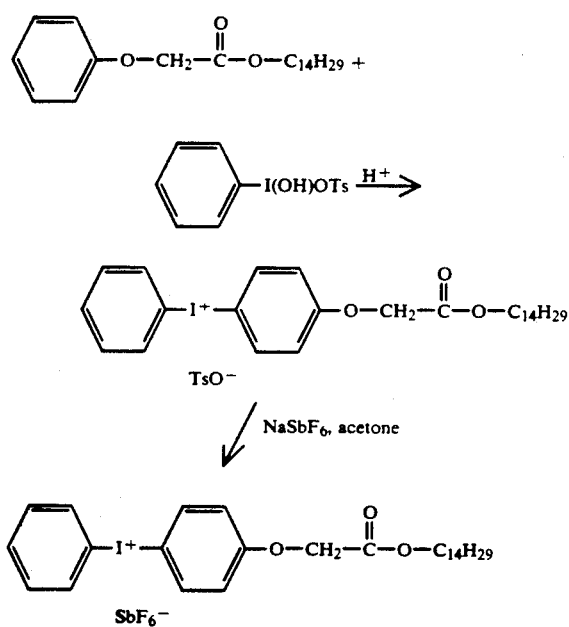

As in the first example, there were placed into a 150 ml Erlenmeyer flask, 20 ml methylene chloride, 7.84 (0.02 mol) hydroxytosyloxy iodobenzene, 10 ml glacial acetic acid and 6.96 g (0.02) mol 1-tetradecyl phenoxyacetate. The mixture was heated to 40° C. in a water bath. Reaction required approximately one hour during which the bulk of the insoluble [hydroxy(tosyloxy)iodo]benzene dissolved. The methylene chloride was removed using a rotary evaporator and to the pale yellow oil was added 30 ml acetone and 5.18 g (0.02 mol) sodium hexafluoroantimonate. Immediate precipitation of sodium tosylate occurred. The salt was removed by suction filtration and the solvent removed from filtrate on a rotary evaporator. The remaining pale yellow oil (12.9 g) was washed with two 100 ml portions of distilled water. One percent solutions of this photoinitiator when dissolved in 4-vinyl cyclohexene dioxide and spread as 1 mil films on glass plates gave cured, tack-free films in 5 seconds when irradiated with a G.E. H3T7 medium pressure mercury arc lamp ballasted at 100 Watts. When a one percent solution of the above photoinitiator was prepared in triethylene glycol divinyl ether, the mixture cured to hard insoluble films after exposure for one second as described above.

EXAMPLE 3 PREPARATION OF

SYNTHESIS OF 3-CHOLESTERYLPHENOXYACETATE
(C$_{35}$H$_{42}$O$_3$, MW=538.6)

Combined were 38.6 g (0.1 mol) cholesterol (C$_{27}$H$_{34}$O), 15.2 g (0.1 mol) phenoxyacetic acid, 0.5 g p-toluenesulfonic acid monohydrate and 70 ml toluene. The reaction mixture was heated to reflux for five hours during which 1.8 g water was collected in a Dean Stark trap. There were isolated after removal of the toluene, 52 g (100% yield) of the ester.

PREPARATION OF THE IODONIUM SALT
(MW=978)

To 7.88 g (0.02 mol) [hydroxy(tosyloxy)iodo]benzene there were added 10.77 g (0.02 mol) of 3-cholesterylphenoxyacetate, 25 ml methylene chloride and 5 ml glacial acetic acid. The reaction mixture was stirred and heated to 40° C. (reflux) for one hour during which all of the solid [hydoxy(tosyloxy)iodo]benzene dissolved. On initial mixing of the components at room temperature a characteristic green color developed as the reaction proceeded. The methylene chloride was removed on a rotary evaporator leaving a yellow-brown oil.

The oil was diluted with 50 ml acetone; and, 5.18 g sodium hexafluoroantimonate was added. Sodium tosylate precipitated on stirring for one hour. After removing the sodium tosylate by filtration, the acetone was evaporated on a rotary evaporator and the remaining mixture of oil and crystals poured into 300 ml distilled water. The product, a light tan colored semisolid, was washed several times with water and on standing tended to crystallize. There were obtained 21.4 g of product. The crude iodonium salt was very active as a photoinitiator and was dissolved as a 0.5% solution in 4-vinylcyclohexene dioxide. Exposure of a one mil film of this mixture to a G.E. H3T7 medium pressure mercury arc lamp ballasted at 200W gave a cured film after a one second irradiation. The iodonium salt was recrystallized using a mixture of isopropanol and water as a recrystallization solvent. The product was a pale yellow crystalline solid (yield 11 g).

The examples disclosed herein are directed to but a few compounds of this new class of diaryliodonium salt photo and thermal initiators. The general description preceeding these examples provides clear insight to the preparation and use of the salts disclosed in the instant invention. It will be observed that these new initiators also have excellent compatability with even such nonpolar monomers as epoxidized oils and poly (1,2-butadiene oxide). These and other utility factors will be discernable by those of ordinary skill practicing the invention and whose interest is further stimulated by the following evidence regarding the solubility and reactivity of the new initiators.

SOLUBILITY EXPERIMENTS

The following experimental activities were carried out to further evidence solubility and reactivity of the diaryliodonium salts of the present invention, as compared to simple diaryliodonium salts described in the earlier art (cf. J. V. Crivello and J. L. Lee, U.S. Pat. No. 4,882,201, Nov. 21, 1989, "Non-Toxic Aryl Onium Salts, UV Curable Coating Compositions and Food Packaging Use." an J. V. Crivello and J. L. Lee, U.S. Pat. No. 4,683,317, Jul. 28, 1987, "Photopolymerizable Organic Compositions and Diaryliodonium Salts Used Therein").

There were prepared one percent (1%) by weight mixtures of the following salts in 2-methyl-1,3-propanediol divinyl ether: diphenyliodonium hexafluoroantimonate (DP), [4(1-octadecylphenoxyacetate)]phenyl iodonium hexafluoroantimonate (OPPA) and (4-octadecyloxyphenyl)phenyl iodonium hexafluoro hexafluoroantimonate (OPP). The three solutions were coated as one (1.0) mil films onto glass plates and exposed to a General Electric H3T7 medium pressure mercury arc lamp at a distance of six inches. The minimum irradiation time required to produce a tack-free coating was recorded.

| PHOTOINITIATOR | TACK-FREE TIME (sec) |
|---|---|
| DP | >50 |
| OPPA | 1.0 |
| OPP | >30 |

Clearly, in this rather typical cationically polymerizable monomer, OPPA is a superior photoinitiator. This photoinitiator contains an ester linkeage attached to the aromatic ring as well as possessing more than 20 carbon atoms in the side chain. In contrast, the diphenyliodonium hexafluoroantimonate (DP) and even the (4-octadecyloxyphenyl) phenyliodonium hexafluoroatimonate analogs are not soluble in the monomer and for this reason fail to cure when these solutions are irradiated.

In another series of tests, it was found that OPPA is soluble in alpha-methylstyrene, while both DP and OPP are not. Alpha-methylstyrene is a well known cationically polymerizable monomer. In this case, only OPPA could be employed to carry out its cationic polymerization.

Thus, the superiority of the photoinitiators of this invention as compared to those of the earlier art in the cure of nonpolar monomers and oligomers is clearly demonstrated.

What is claimed is:

1. A process for making diaryliodonium salt photo/thermal initiators for cationic polymerization which have solubilities greater than diaryliodonium salts possessing carbon groups of 20 carbon atoms and less, said process comprising the steps of:
   a) esterfying a monoaryl acid to produce a monoaryl ester of the form $$\text{C}_6\text{H}_5\text{—O—CR}_2\text{—}\overset{\text{O}}{\underset{\|}{\text{C}}}\text{—O—C}_n\text{H}_{2n+1}$$

R representing hydrogen, aryl, alkyl or a halide; and
   b) reacting said ester with hydroxy(tosyloxy)iodobenzene in the presence of an organic solvent and thereafter with a metal halide to produce said diaryliodonium salt comprising a long chain ester function concatenated with an aryl group of said acid in said esterfying step with more than 20 carbon atoms in said concatenated function/group and of the form:

$$\text{C}_6\text{H}_5\text{—}\underset{\text{X}^-}{\text{I}^+}\text{—C}_6\text{H}_4\text{—O—CR}_2\text{—}\overset{\text{O}}{\underset{\|}{\text{C}}}\text{—O—C}_n\text{H}_{2n+1}$$

wherein n is such that the total number of carbon atoms is greater than 20, and $X^-$ is a complex metal halide anion.

2. The process of claim 1 wherein $X^-$ is a complex metal halide anion such as $BF_4^-$, $PF_6^-$, $AsF_6^-$, and $SbF_6^-$.

3. The process of claim 2 wherein $X^-$ further comprises anions of strong protonic acids.

4. A diaryiodonium salt for photo/thermal initiation of cationic polymerization of such monomers as mono-, di- and polyfuctional epoxides, said salt characterized by the general formula:

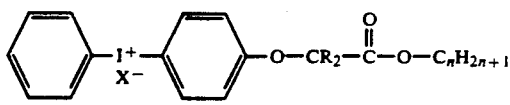

where:
R is hydrogen, aryl, alkyl or an halide;
n is an integer such that the total number of carbon atoms included by the entire moiety appended to the iodine atom is greater than 20; and
$S^-$ is a complex metal halide anion.

5. The diaryliodonium salt of claim 4 wherein $X^-$ further comprises a complex halide anion of a strong protonic acid.

6. A photo/thermal polymerization initiator that is soluble in 2-methyl-1,3-propanediol divinyl ether and alphamethylstyrene monomers and is characterized as a diaryliodonium group having contatenated therewith an aliphatic group wherein a total of 21 or more carbon atoms comprise the aryl/aliphatic groupings.

7. A method for making the initiator of claim 6 comprising reacting a monoaryl ester of the form

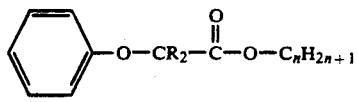

n being an integer such that the ester contains at least 15 carbon atoms, R representing hydrogen, aryl, alkyl or a halide, with [hydroxy(tosyloxy)iodo]benzene in the presence of an organic solvent and a metal halide capable of imparting a complex halide anion to said initiator.

* * * * *